United States Patent [19]

Tabibi et al.

[11] Patent Number: 5,039,527

[45] Date of Patent: Aug. 13, 1991

[54] HEXAMETHYLMELAMINE CONTAINING PARENTERAL EMULSIONS

[75] Inventors: Esmail Tabibi, Chelmsford; Arthur A. Siciliano, Framingham, both of Mass.

[73] Assignee: MediControl Corporation, Newton, Mass.

[21] Appl. No.: 314,954

[22] Filed: Feb. 24, 1989

[51] Int. Cl.[5] .............................................. A61K 37/22
[52] U.S. Cl. .................................... 424/450; 514/946; 514/947; 514/825; 514/826
[58] Field of Search ................ 424/450; 514/947, 946, 514/825, 826

[56] References Cited

U.S. PATENT DOCUMENTS 4,537,776 8/1985 Cooper ................................. 514/947
4,557,934 12/1985 Cooper ................................. 514/859

Primary Examiner—Page Thurman K.
Assistant Examiner—W. E. Benston, Jr.
Attorney, Agent, or Firm—Bruce F. Jacobs

[57] ABSTRACT

Improved hexamethylmelamine containing parenteral emulsions are prepared in the absence of organic solvents and containing low levels of biocompatible emulsifiers using ultrahigh energy Microfluidizer ® processing equipment. The emulsions have oil phase droplets with average diameters of less than about 0.4 microns with size distributions of less than about +/−50%.

14 Claims, No Drawings

HEXAMETHYLMELAMINE CONTAINING PARENTERAL EMULSIONS

BACKGROUND OF THE INVENTION

This invention relates generally to oil-in-water emulsions suitable for the parenteral administration of the lipophilic anticancer drug hexamethylmelamine (HMM) and their method of preparation. More specifically it relates to such emulsions which are suitable for intravenous administration in humans and which contain submicron sized oil phase droplets having a narrow size range and which are prepared in the substantial absence of any organic solvents by means of particular ultra high energy mixing equipment known as Microfluidizer ® processing equipment.

The uniform submicron sized emulsions of the present invention offer substantial advantage over prior delivery methods. HMM is an antitumor agent which has shown activity against several human malignancies in clinical trials for over 20 years. However its use has been limited because HMM exhibits low water solubility and good oil solubility. Due to this solubility combination, there has heretofore been a lack of a satisfactory parenteral preparation. As a result the clinical trials have been performed by oral administration of solid dosage forms which has resulted in low and/or variable plasma concentrations of the drug.

Recognizing the problem, others have made several attempts at converting HMM to a water-soluble salt, but when such a product was administered parenterally, it produced local irritation, venous thrombosis, and phlebitis. Recent reviews of this include D. Hahn, Drug Intelligence and Clin. Pharmacy 17: 418 (1983) and H. Van-Zutphen, Pharmaceutisch Weekblad 4:25 (1982).

HMM has previously been reported by both M. Ames et al (Cancer Treatment Reports 66:1579 (1982) and A. Wickes et al (Cancer Treatment Reports 69:657 (1985)) to have been administered parenterally using emulsion carriers. These products were prepared by adding solid HMM crystals directly into a commercial parenteral feeding emulsion (Intralipid ™, Cutter Labs, Berkeley, Calif.) or by dissolving the crystals in a solvent such as ethanol or di methylacetamide and then adding this solution to the Intralipid. Such, emulsion forming methods are not suitable for commercial preparations of HMM since they could cause severe problems due to, for instance, incomplete dissolution of the HMM, the presence of harsh organic solvents which is contraindicated, the widely variable resulting droplet size range, the excessive injection volume required, and product instability and biocompatability problems due to the presence of meaningful amounts of larger droplets (>1 micron).

Accordingly, it is the object of the present invention to produce a stable oil-in-water emulsion containing HMM in the oil phase which emulsion is suitable for the parenteral administration of HMM to humans and in which substantially all of the oil droplets are of submicron size and also have a narrow size distribution. It is a further object of this invention to produce such emulsions in the absence of organic solvents. It is a further object of this invention to utilize low levels of biocompatible emulsifiers. It is a still further object of this invention to produce emulsions which will be storage stable for extended periods, easily sterilized, easily preserved, economically produced, and showing improved efficacy, reduced irritation and an improved therapeutic ratio.

SUMMARY OF THE INVENTION

It has been discovered that an oil-in-water emulsion may be prepared comprising a continuous aqueous phase having distributed therein discontinuous oil phase particles, having average diameters of less than about 0.4 microns and containing dissolved therapeutic amounts of the anticancer agent, hexamethylmelamine. The emulsion is substantially free of organic solvents and may be prepared by means of Microfluidizer ® ultra high energy processing. The emulsion comprises a combination of about 5 to about 50% of a lipidic material suitable for parenteral administration to humans, from about 0.01 to about 1.0% of hexamethylmelamine, from about 0.1 to about 50% of biocompatible emulsifiers, and the balance, i.e. from about 40 to about 90%, water, wherein all percents are by weight. Optionally, other water-soluble, amphiphilic or lipidic compounds may be present including other anticancer agents.

DESCRIPTION OF THE PREFERRED EMBODIMENTS

Oil-in-water hexamethylmelamine containing emulsions suitable for parenteral use in accordance with the present invention are formed in the absence of organic solvents using Microfluidizer processing equipment. The oil phase particles have average diameters less than about 0.4 microns, preferably less than about 0.3 microns, with a particle size distribution of less than about +/−50%, preferably less than about +/−30%.

Generally, the emulsion comprises about 5 to about 50 wt % of one or more lipidic materials, about 0.01 to about 1 wt % hexamethylmelamine, about 0.1 to about 10 wt % one or more emulsifiers, and about 40 to about 95 wt % water. More preferably, the emulsion comprises about 5 to about 35 wt % lipidic material, about 0.05 to about 0.75 wt % hexamethylmelamine, about 0.2 to about 5.0 wt % emulsifier and about 60 to about 95 wt % water. Most preferably, the emulsion is comprised of about 10 to about 20 wt % lipidic materials, about 0.1 to about 0.5 wt % hexamethylmelamine, about 0.5 to about 2.0 wt % emulsifiers and about 78 to about 90 wt % water. The emulsions may further contain such conventional parenteral additives as antioxidants, buffers, preservatives, stabilizers, electrolytes, isotonicity agents, viscosity modifiers, as well as non-interfering other anticancer agents.

The lipidic materials useful herein include, but are not limited to, parenterally acceptable vegetable and fish oils, triglycerides, synthetic or semi-synthetic mono, di, or triglycerides, and any other lipidic material generally recognized as safe and suitable for the intended use.

The anticancer agent hexamethylmelamine (HMM) has the formula $C_9H_{18}N_6$ and a Chemical Abstracts name of 1,3,5-triazine-2,4,6-triamine-N,N,N',N',N'',N''-hexamethyl. It has a relative molecular mass of about 210.3 Daltons. It is generally prepared by reacting dimethylamine and sodium hydroxide aqueous solutions with cyanuric acid in acetone. Further details regarding its preparation may be found in the literature (Wortzalla, J. F. et al., Cancer Res., 33:2810 (1973)) as the present invention is independent of the method of preparation of HMM.

Oil-in-water emulsifiers suitable for use herein include those surface active agents which are capable of forming oil-in-water emulsions and suitable for parenteral use. Examples of such emulsifiers include, but are not limited to, such as natural and synthetic phospholipids, egg and soy lecithins, block copolymers or propylene and ethylene oxide (Pluronics ™—BASF Corp.), straight chain polyoxyethylene sugar esters (Tweens ™—ICI Americas), sorbitan esters (Arlacels ™—ICI Americas), cholic acid derivatives and the like.

The aqueous phase of the emulsion encompasses the usual suitable parenteral grades of water.

The lipidic and aqueous phases may each also contain other components known to the art to be appropriate for the preparation and/or use of parenteral compositions. Examples of such materials include antioxidants, stabilizers, buffers, preservatives, electrolytes, isotonicity agents, viscosity modifiers, and other anticancer agents. Further details of these materials may be found in the literature as they have not been found to be critical to the present invention.

The oil-in-water emulsion is prepared by (i) forming a lipidic solution by dissolving all lipid-soluble components, lipophilic emulsifiers, and the HMM into the lipidic materials, (ii) forming an aqueous solution by dissolving all of the water-soluble additives and hydrophilic emulsifiers into the water, (iii) forming an initial crude oil-in-water emulsion of the two phases by adding the lipidic solution to the aqueous solution, or the reverse addition, with generally low energy mixing, and (iv) subjecting the initial crude emulsion to an ultra high energy mixing device to reduce the size of the oil phase droplets until they have an average diameter of less than about 0.4 microns and the desired narrow size distribution. Heat may be used to accelerate dissolution of either or both the lipidic and aqueous phases, provided that none of the components in the heated phase is subject to heat degradation.

Critical to the preparation of the oil-in-water emulsions containing oil phase droplets having an average diameter of less than about 0.4 microns, preferably less than 0.3 microns, with a narrow size distribution in the range of less than +/−50%, preferably less than +/−30%, is the use of an ultra high energy mixing technology. Conventional mixing technology is seldom able to achieve such a small size and narrow size distribution without employing unacceptably high levels of emulsifiers, solvents and the like. The preferable oil droplet size and size distribution range may be readily achieved by employing a process exemplified by Microfluidizer technology. Microfluidizer ® equipment is commercially available from Microfluidics Corp., Newton Mass., and is described in U.S. Pat. No. 4,533,254, the subject matter of which is hereby incorporated by reference.

To utilize the Microfluidizer equipment and technology, a coarse emulsion is prepared by slowly adding one phase to the other, preferably the aqueous phase to the lipid phase, with low energy mixing provided by such equipment as a conventional propeller stirrer. The crude emulsion is then processed through the ultra high energy Microfluidizer equipment to produce the superfine oil-in-water emulsion of submicron size of the present invention and having a narrow size distribution. This microemulsion exhibits excellent storage stability with regard to retaining its initial average droplet size and size distribution. The microemulsion is sufficiently stable that it may be subjected to further manipulations, such as sterilization and packaging as are well known in the art, without causing coagulation or deemulsification.

The practice of this invention is illustrated by, but not limited to, the following examples in which all parts and percents are by weight unless otherwise specified.

EXAMPLE I

In a suitable container 0.5 gm of hexamethylmelamine (National Cancer Institute, Bethesda, Md.) is dissolved in 15.0 g of soybean oil, USP, superfine (Welch, Holme, and Clarke; S. Plainfield, N.J.) by propeller mixing. To this solution is slowly added 1.2 g of egg phospholipid, parenteral grade (Pfanstiehl; Waukegan, Ill.) while mixing is continued. In another container, 0.5 g of Pluronic ™ F-68 surfactant (BASF; Parsippany, N.J.) and 2.25 g of glycerin, USP (Fisher; Pittsburgh, PA) is dissolved in 40 ml of water for injection, USP (Baxter; Morton Grove, Ill.) using propeller mixing. The aqueous solution is then slowly added to the lipidic solution while propeller mixing continues, the pH adjusted to 7.4 with reagent grade hydrochloric acid or sodium hydroxide as necessary, and the total volume is adjusted to 100 ml with water for injection. The coarse emulsion so obtained (droplet size ranging from about 2 to 25 microns) is then processed through a Microfluidizer ® M-110 (Microfluidics; Newton, Mass.) three times at 12,000 psi operating pressure. The resulting droplet size of the microemulsion was measured using a quasielastic laser light scattering particle size determination instrument (Brookhaven; Model BI-90, Brookhaven, N.Y.). The average droplet size was 0.22 microns with a size distribution of +/−26%. The emulsion was then packaged into suitable parenteral containers and sterilized by autoclaving at 121° C. for 15 minutes. Particle size was then measured again and was found to be 0.20 microns with a size distribution of +/−29%. The stability of this emulsion was then evaluated by centrifugation for 30 minutes at 3000RPM—no separation was observed. Shelf life was evaluated by visual examination after 10 months' storage at room temperature (23° C.). No untoward effects were seen. A particle size measurement on this stored sample showed average diameters of 0.25 microns with a size distribution of +/−23%.

EXAMPLE II

A coarse emulsion was prepared as in Example I except that 0.2 g of hexamethylmelamine was used. It was then processed through a Microfluidizer M-110 three times at 10,000 psi operating pressure and then suitably packaged and sterilized. The resulting droplet size of the microemulsion measured 0.9 microns with a size distribution of +/−25%. After 11 months' storage at room temperature, the product measured 0.24 microns with a size distribution of +/−21%.

EXAMPLE III

A coarse emulsion was prepared as in Example II except that the Pluronic F-68 surfactant was omitted. It was then processed three times through a Microfluidizer M-110 at 14,000 psi operating pressure. The resulting droplet size of the microemulsion measured 0.27 microns with a size distribution of +/−28%. After suitable packaging, the emulsion was sterilized. The particle size was determined to be 0.3 microns with a size distribution of +/−31%.

EXAMPLE IV

A coarse emulsion was prepared as in Example III except that 0.3 g of hexamethylmelamine was used. It was then processed through a Microfluidizer M-110 three times at 14,000 psi operating pressure. The resulting droplet size of the microemulsion was 0.24 microns with a size distribution of +/−30%. After suitable packaging and sterilization, the size was determined to be 0.29 microns with a size distribution of +/−24%.

EXAMPLE V

A coarse emulsion was prepared as in Example III except that 0.4 g of hexamethylmelamine was used. It was then processed through a Microfluidizer M-110 three times at 15,000 psi. The resulting droplet size of the microemulsion measured 0.26 microns with a size distribution of +/−26%. After suitable packaging and sterilization, the droplet size measured 0.31 microns with a size distribution of +/−33%.

EXAMPLE VI

A coarse emulsion was prepared as in Example III except that 0.5 g of hexamethylmelamine was utilized. It was then processed through a Microfluidizer M-110 three times at 15,000 psi. The resulting droplet size of the microemulsion measured 0.23 microns with a size distribution of +/−32%. After suitable packaging and sterilization, the droplet size measured 0.40 microns with a size distribution of +/−38%.

What is claimed is:

1. An oil-in-water emulsion for the administration of hexamethylmelamine which consists essentially of a continuous aqueous phase and a discontinuous oil phase, wherein said oil phase comprises droplets having an average diameter of less than about 0.4 microns with a size distribution of less than about +/−50%, wherein the emulsion comprises
   about 5 to about 50 weight percent of one or more lipidic materials which may contain dissolved therein one or more lipophilic compounds selected from the group consisting essentially of antioxidants, preservatives, vitamins, stabilizers, and anticancer agents,
   about 0.01 to about 1.0 weight percent hexamethylmelamine,
   about 0.1 to about 10 weight percent of one or more emulsifiers, and
   about 40 to about 95 weight percent water which may contain dissolved therein one or more water-soluble materials selected from the group consisting essentially of buffers, preservatives, electrolytes, isotonicity agents, viscosity modifiers, stabilizers, vitamins, amino acids, and anticancer agents,
   and wherein the emulsion is parenterally administered to a patient.

2. The emulsion of claim 1 wherein the lipidic material is selected from the group consisting essentially of parenterally acceptable vegetable and fish oils, triglycerides, and semisynthetic mono, di, and triglycerides.

3. The emulsion of claim 1 wherein the emulsifier is selected from the group consisting essentially of natural and synthetic phospholipids, egg and soy lecithins, block copolymers of ethylene and propylene oxide, straight chain polyoxethylene sugar esters, sorbitan esters, and cholic acid derivatives.

4. The emulsion of claim 1 wherein the emulsifier comprises a phospholipid-containing emulsifier derived from eggs.

5. The emulsion of claim 1 wherein the emulsifier comprises a phospholipid containing emulsifier derived from soybeans.

6. The emulsion of claim 1 wherein the droplets are less than about 0.3 microns in average diameter with a size distribution of less than +/−30%.

7. The emulsion of claim 1 wherein the emulsion consists essentially of about 5 to about 35 weight % of one or more lipidic materials, about 0.05 to about 0.75 weight % hexamethylmelamine, about 0.2 to about 5.0 weight % of one or more emulsifiers, and about 60 to about 95 weight % water.

8. The emulsion of claim 1 wherein the emulsion consists essentially of about 10 to about 20 weight % of one or more lipidic materials, about 0.1 to about 0.5 weight % hexamethylmelamine, about 0.5 to about 2.0 weight % of one or more emulsifiers, and about 78 to about 90 weight % water.

9. The emulsion of claim 1 in the substantial absence of any organic solvents

10. A method of preparing the oil-in-water emulsion of claim 1 which comprises (i) forming a lipidic solution by dissolving all lipid-soluble components, lipophilic emulsifiers, and the hexamethylmelamine into the lipidic materials, (ii) forming an aqueous solution by dissolving all of the water-soluble additives and hydrophilic emulsifiers into the water, (iii) forming an initial crude oil-in-water emulsion of the two phases by addition of the lipidic solution to the aqueous solution with mixing, and (iv) subjecting the initial crude emulsion to an ultra high energy mixing device to reduce the size of the oil phase droplets until they have an average diameter of less than about 0.4 microns and to reduce the size distribution of said droplets to +/−50%.

11. The method of claim 10 wherein the ultra high energy mixing device is a Microfluidizer device.

12. The method of claim 10 wherein the device is operated at an internal pressure of about 2,000 to about 20,000 psi.

13. The method of claim 10 wherein the oil phase droplets of the microemulsion have an average diameter of less than about 0.3 microns and a size distribution of less than about +/−30%.

14. The method of claim 10 wherein the initial crude emulsion is formed by addition of the aqueous solution to the lipidic solution with mixing.

* * * * *